(12) United States Patent
Erickson

(10) Patent No.: US 7,527,610 B2
(45) Date of Patent: May 5, 2009

(54) CONNECTION INDICATOR FOR A MEDICAL DELIVERY/EXTRACTION SYSTEM

(75) Inventor: Dean A. Erickson, Greenfield, WI (US)

(73) Assignee: BioForm Medical, Inc., San Mateo, CA (US)

(*) Notice: Subject to any disclaimer, the term of this patent is extended or adjusted under 35 U.S.C. 154(b) by 499 days.

(21) Appl. No.: 10/113,680

(22) Filed: Mar. 29, 2002

(65) Prior Publication Data

US 2003/0187409 A1    Oct. 2, 2003

(51) Int. Cl.
*A61M 5/00* (2006.01)

(52) U.S. Cl. ............................ 604/240

(58) Field of Classification Search ........... 604/240, 604/263, 198, 181, 241, 187, 189, 110
See application file for complete search history.

(56) References Cited

U.S. PATENT DOCUMENTS

| | | | |
|---|---|---|---|
| 387,454 A | 8/1888 | Siegenthaler | |
| 3,391,694 A | 7/1968 | Spaeth | 128/218 |
| 3,450,135 A | 6/1969 | Samoff | 128/221 |
| 3,628,524 A | 12/1971 | Jamshidi | 128/2 B |
| 3,630,192 A | 12/1971 | Jamshidi | 128/2 B |
| 3,662,457 A | 5/1972 | Gores | 29/508 |
| 3,670,727 A | 6/1972 | Reiterman | |
| 3,727,613 A * | 4/1973 | Sorenson et al. | 604/165.02 |
| 4,013,080 A * | 3/1977 | Froning | 604/165.01 |
| 4,233,974 A | 11/1980 | Desecki et al. | 128/215 |
| 4,237,882 A | 12/1980 | Wickham | |
| 4,256,119 A | 3/1981 | Gauthier | 128/754 |
| 4,266,555 A | 5/1981 | Jamshidi | 128/753 |
| 4,340,066 A | 7/1982 | Shah | 128/749 |
| 4,396,021 A | 8/1983 | Baumgartner | 128/754 |
| 4,403,617 A | 9/1983 | Tretinyak | 128/754 |
| 4,430,080 A | 2/1984 | Pasquini et al. | 604/240 |
| 4,445,893 A | 5/1984 | Bodicky | 604/165 |
| 4,518,383 A | 5/1985 | Evans | 604/51 |
| 4,573,978 A | 3/1986 | Reilly | 604/240 |
| 4,609,370 A | 9/1986 | Morrison | 604/165 |
| 4,642,103 A | 2/1987 | Gettig | 604/234 |
| 4,655,226 A | 4/1987 | Lee | 128/754 |
| 4,667,684 A | 5/1987 | Leigh | 128/754 |
| 4,668,226 A | 5/1987 | Omata et al. | 604/272 |
| 4,758,218 A | 7/1988 | Kiefer et al. | 604/53 |
| 4,799,495 A | 1/1989 | Hawkins et al. | 128/754 |
| 4,838,282 A | 6/1989 | Strasser et al. | 128/754 |
| 4,842,592 A | 6/1989 | Caggiani et al. | 604/283 |
| 4,844,087 A | 7/1989 | Garg | 128/753 |
| 4,846,804 A | 7/1989 | Davis et al. | 604/164 |
| 4,881,551 A | 11/1989 | Taylor | 128/754 |
| 4,889,529 A | 12/1989 | Haindl | 604/274 |
| 4,923,447 A | 5/1990 | Morgan | 604/198 |
| 4,967,762 A | 11/1990 | DeVries | 128/753 |
| 5,005,585 A | 4/1991 | Mazza | 128/754 |

(Continued)

*Primary Examiner*—Nicholas D Lucchesi
*Assistant Examiner*—Victoria P Campbell
(74) *Attorney, Agent, or Firm*—Foley & Lardner LLP (57) ABSTRACT

A medical delivery or extraction system comprising a needle assembly having a needle and a hub coupled to the needle. The hub includes a verification region or component. A syringe body rotatably coupled to the needle assembly includes at least one indicia on the outer surface thereof. When the indicia corresponds to the verification region, the user is provided with an indication that the se body is properly connected to the needle assembly.

26 Claims, 5 Drawing Sheets

U.S. PATENT DOCUMENTS

| | | | |
|---|---|---|---|
| 5,026,355 A | 6/1991 | Sweeney et al. | 604/243 |
| 5,031,634 A | 7/1991 | Simon | 128/754 |
| 5,059,186 A | 10/1991 | Yamamoto et al. | 604/280 |
| 5,061,251 A | 10/1991 | Juhasz | 604/198 |
| 5,078,690 A | 1/1992 | Ryan | 604/187 |
| 5,081,997 A | 1/1992 | Bosley, Jr. et al. | 128/662.02 |
| 5,205,833 A | 4/1993 | Harsh et al. | 604/240 |
| 5,226,898 A | 7/1993 | Gross | 604/243 |
| 5,242,405 A | 9/1993 | Howe | 604/125 |
| 5,328,466 A | 7/1994 | Demark | 604/93 |
| 5,336,191 A | 8/1994 | Davis et al. | 604/165 |
| 5,385,561 A | 1/1995 | Cerny | 604/264 |
| 5,716,346 A | 2/1998 | Farris | 604/243 |
| 5,782,505 A | 7/1998 | Brooks et al. | 285/175 |
| 5,833,674 A | 11/1998 | Turnbull et al. | 604/283 |
| 5,860,955 A | 1/1999 | Wright et al. | 604/99 |
| 5,941,853 A | 8/1999 | Collins | 604/165 |
| 6,063,057 A | 5/2000 | Choh | 604/99 |
| 6,132,402 A | 10/2000 | Tessmann et al. | 604/240 |
| 6,167,886 B1 | 1/2001 | Engel et al. | 128/885 |
| 6,210,372 B1 | 4/2001 | Tessmann et al. | 604/181 |
| 6,280,430 B1 | 8/2001 | Neftel et al. | 604/411 |
| 6,565,550 B1 | 5/2003 | Klein et al. | |
| 6,966,897 B2 | 11/2005 | Shimazaki | |
| 2003/0195479 A1* | 10/2003 | Kuracina et al. | 604/263 |

* cited by examiner

CONNECTION INDICATOR FOR A MEDICAL DELIVERY/EXTRACTION SYSTEM

FIELD OF THE INVENTION

The present invention is directed to medical delivery/extraction systems. More particularly, the present invention is related to a medical delivery/extraction system with a built-in indicator of whether individual components of the system are properly connected to each other.

BACKGROUND OF THE INVENTION

Syringe and needle assemblies have been used for a number of years for the purpose of injecting fluids into or withdrawing fluids from a body. These fluids may include medicine, blood or other types of biological materials. Due to the multitude of infectious diseases which may be carried by bodily fluids such as blood, it is extremely important that any potential leakage of fluid during an injection or withdrawal process be kept to an absolute minimum.

One location in a delivery/extraction system where bodily fluids and/or other substances may leak from the system is the connection area between the syringe and the needle assembly. Because syringes and needle assemblies are often marketed and/or manufacture separately, a doctor, nurse or other technician is required to properly connect the needle assembly to the syringe. If the needle assembly is not properly connected to the syringe, the possibility of a poor connection and accidental leakage of biological materials increases significantly. This correspondingly increases the risk of exposure to hazardous materials.

The type of media being delivered out of the syringe may also contain materials, components, or ingredients that can separate at a poor connection when exposed to the injection pressures developed in the syringe. The material separation can cause further problems of injecting or extracting the full contents of the syringe through the needle. A properly connected needle assembly to the syringe would significantly reduce the possibility of material, component, or ingredient separation from occurring.

A variety of mechanisms have been developed to securely fasten needle assemblies to syringes, but each have their drawbacks. For example, a number of conventional mechanisms include a linear connection between the syringe and the needle assembly in the form of a track or groove, in which the needle assembly slides onto the syringe. Systems with linear connections often include o-ring type seals that are located a certain distance from the path of the fluid material. This distance between the seal and the material pathway may cause delivery and/or extraction problems for certain types of materials. Other types of conventional systems involve a rotational fitting between the needle assembly and the syringe. These systems allow for a line-to-line seal that is integral to the material path, but the systems are somewhat limited in their ability to indicate to the user when an adequate or proper connection has been achieved. Furthermore, some of these systems may be prone to being "overtightened" which can affect the functionality and/or safety of the completed assembly. Also, it can often be difficult to determine whether the needle assembly is properly connected to the syringe. In either case, an improperly made connection between the needle assembly and the syringe can have hazardous results and/or functional/operational problems.

SUMMARY OF THE INVENTION

It is therefore an object of the invention to provide an improved delivery or extraction system that provides a simple mechanism for ensuring a proper connection between components.

It is another object of the invention to provide an improved delivery or extraction system that includes a mechanism to indicate to a user that a proper connection has been achieved.

It is still another object of the invention to provide an improved delivery or extraction system that minimizes the incidence of fluids escaping from the system.

It is yet another object of the present invention to provide an improved delivery and extraction system that provides a visual indication of whether an adequate or proper connection has been made in the system.

It is another object of the present invention to provide an improved delivery and extraction system that is simple to use while still maintaining a high degree of safety.

It is finally another object of the present invention to provide an indicator means that provides accurate and concurrent positioning of both linear and angular orientation, ensuring indication of a proper connection.

In accordance with the above objects, a medical delivery and extraction system is provided. The system comprises a needle assembly including a needle with a hub formed therein. A syringe body is rotatably coupled to the needle assembly. The syringe body includes at least one indicia on a portion of the body, and the needle hub includes a verification region an a portion thereof. The indicia and verification region are arranged on the syringe body and needle hub, respectively, such that when the syringe body is properly fastened to the needle assembly, the indicia aligns with the verification region, giving the user an indication that the needle assembly is properly connected to the syringe body.

BRIEF DESCRIPTION OF THE DRAWINGS

The foregoing advantages and features of the invention will become apparent upon reference to the following detailed description and the accompanying drawings, of which.

DETAILED DESCRIPTION OF THE INVENTION

A medical delivery or extraction system is shown generally at 100 in FIGS. 1-4. The medical delivery or extraction system 100 comprises a syringe 102 and a needle assembly 104. The syringe 102 comprises a syringe body 110 coupled to an end-piece 112 (see FIG. 2). The syringe body 110 includes a plunger receiving end 114 and a needle assembly receiving end 116. The plunger receiving end 114 is open such that it may accept a plunger 128 that is used to force fluid into or out of the syringe 102. The syringe body 110 also includes a plurality of volume indicia 118 for measuring the amount of fluid inside the syringe 102 at any given moment.

Figure 1:
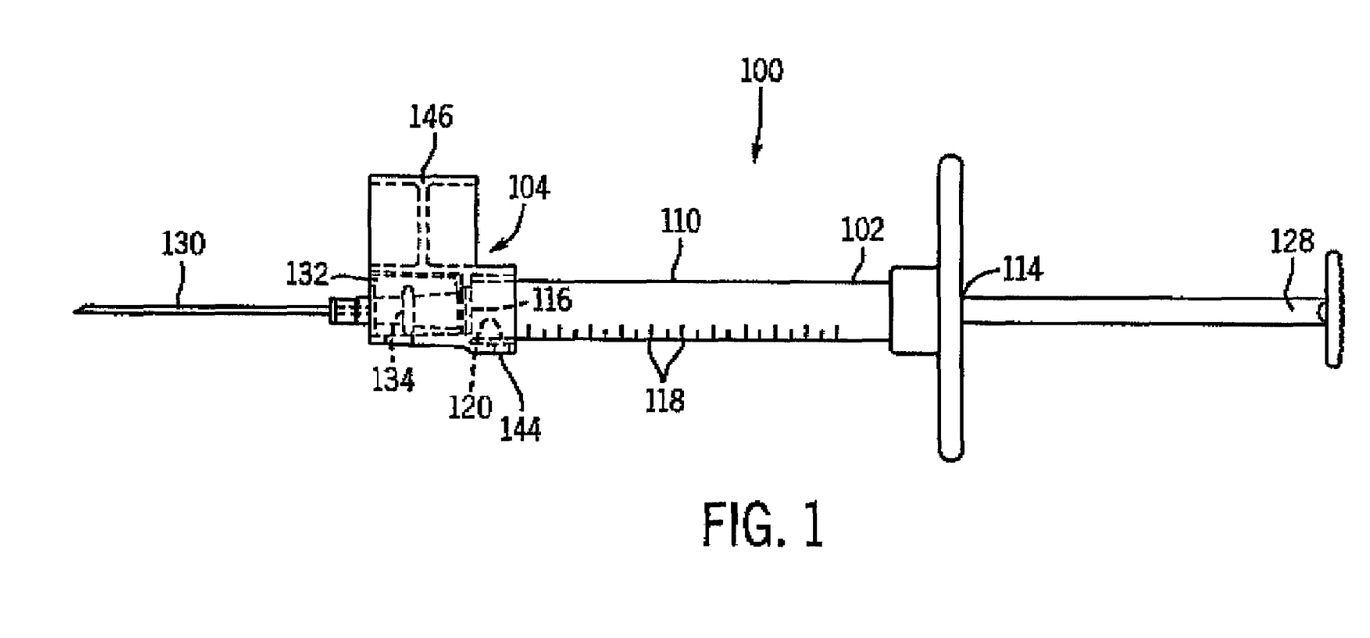
FIG. 1 is a side view of a medical delivery system according to one embodiment of the invention.
Figure 2:
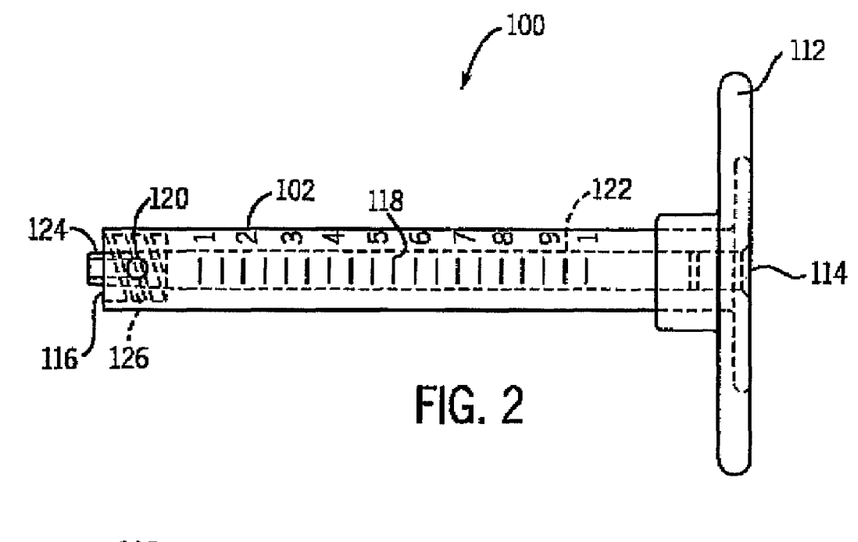
FIG. 2 is a detailed side view of a syringe according to one embodiment of the present invention.

The syringe 102 also includes an inner body 122 on the inside of the syringe 102. The inner body 122 comprises a passageway through which the fluid primarily flows. The inner body 122 terminates at a connection portion 124. In the area around the connection portion 124, there are a plurality of threads 126 formed on the inside of the syringe body 110.

An indicator mark 120 is also included at the needle assembly receiving end 116 of the syringe 102. The indicator mark 120 is used to determine whether the syringe 102 is properly connected to the needle assembly 104. The indicator mark 120 may take a variety of forms. In a preferred embodiment of the invention, the indicator mark 120 comprises a colored dot which is visible by a user. The indicator mark 120 can take a variety of other forms, however, including lines, figures, numbers, colored bands, etc. and a variety of indicating methods including aligning lines or figures, compression rings, etc. Additionally, it is also possible for the indicator mark simply to be a color opposite that of the surrounding portion of the syringe body 110 or to be reverse printed from that described in this embodiment. Furthermore, it is possible to have multiple color bands or other mechanisms for indicating varying degrees of making the connection. The indicator mark 120 can be imprinted on the outer surface of the syringe body 110 or can be imbedded inside the syringe body 110. Furthermore, the indicator mark 120 can comprise a depression, ridge, or groove which mates with the needle assembly 104.

The needle assembly 104 comprises a needle 130 (shown in phantom in FIGS. 3 and 4) coupled to a luer connection 132. The luer connection 132 includes a hub 134 formed on the inside thereof. The hub 134 is hollow and runs from a first end 136 to a second end 138. The hub 134 is sized to accept the needle 130 in a snug relationship. The hub 134, in one embodiment of the invention, also includes a hub ridge 142 at the second end 138. Alternatively, the hub 134 may include a plurality of hub threads 170, shown best in FIGS. 10-14. As shown in FIGS. 1-4, the hub ridge 142 and/or the hub threads 170 are used to mate the needle assembly 104 with the syringe 102. The luer connection 132 also includes a gripping portion 146. The gripping portion 146 may be used by a user to fasten and unfasten the needle assembly 104 from the syringe 102.

Figure 3:
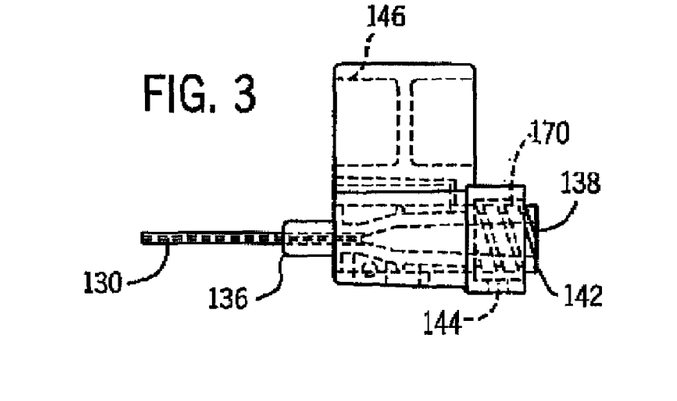
FIG. 3 is a detailed side view of a needle assembly for mating with the syringe of FIG. 2.
Figure 4:
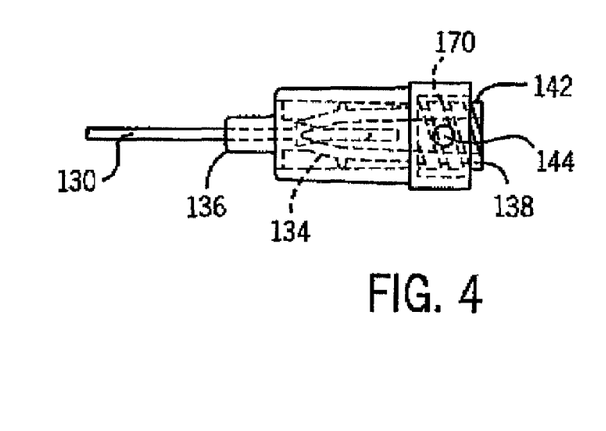
FIG. 4 is a detailed side view of a portion of the needle assembly of FIG. 3 rotated ninety degrees.

The luer connection 132 also includes a viewing region 144. In a preferred embodiment of the invention, the viewing region 144 comprises a circular opening. It is also possible for the viewing region 144 to comprise a transparent material. The viewing region is used by the user to determine if the needle assembly 104 is properly connected to the syringe 102. As is explained herein, when the indicator mark 120 of the syringe 102 is clearly visible through the viewing region 144, then it is understood that the syringe 102 is properly connected to the needle assembly 104.

Figure 10:
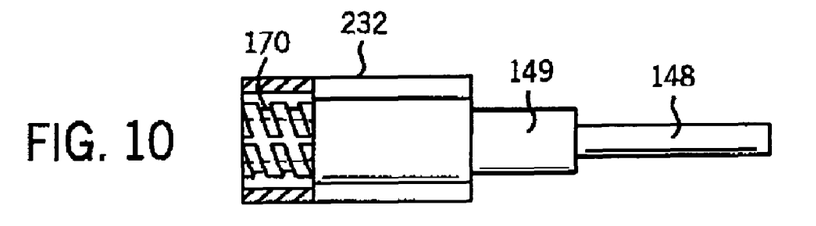
FIG. 10 is a side view of a luer connection according to another embodiment of the invention.
Figure 11:
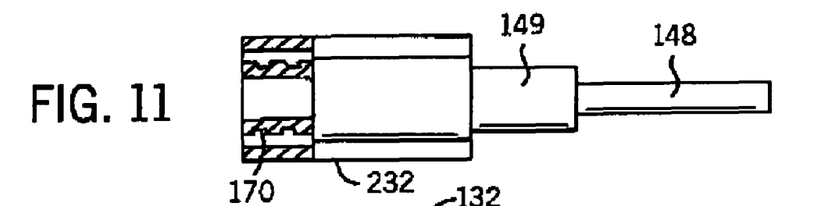
FIG. 11 is another side view of the luer connection of FIG. 10.
Figure 12:
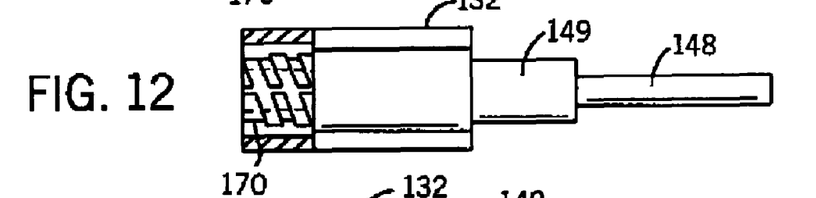
FIG. 12 is a side view of a modified luer connection according to still another embodiment of the invention.
Figure 13:
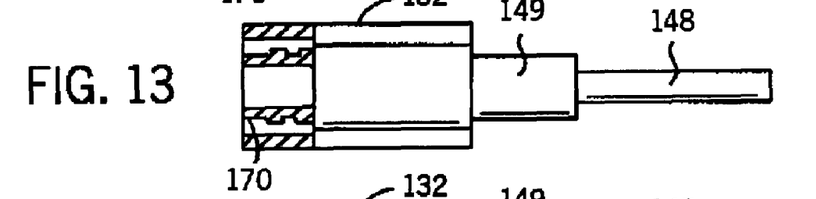
FIG. 13 is a side view of a modified luer connection according to yet another embodiment of the invention.
Figure 14:
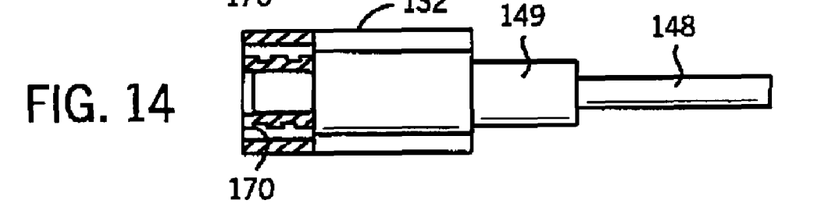
FIG. 14 is a side view of a modified luer connection according to still another embodiment of the invention.
Figure 15:
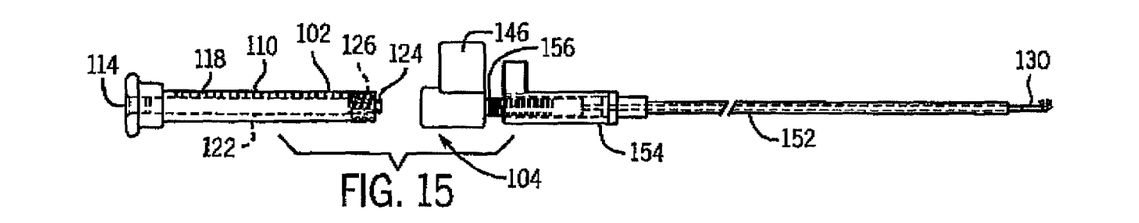
FIG. 15 is a side view of an unfastened medical delivery system including a protective sheath.
Figure 16:
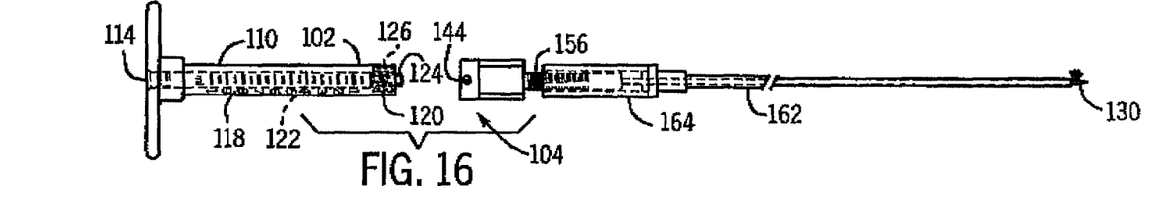
FIG. 16 is a side view rotated ninety degrees of an unfastened medical delivery/extraction system including a cannula.
Figure 17:
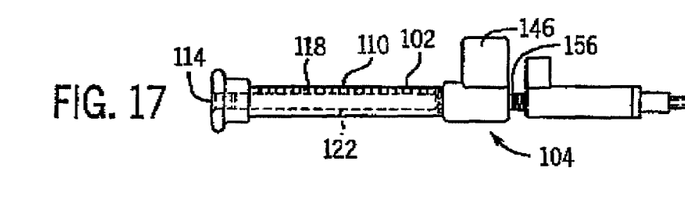
FIG. 17 is a side view rotated ninety degrees of the medical delivery system of FIG. 16 during the securing process.
Figure 18:
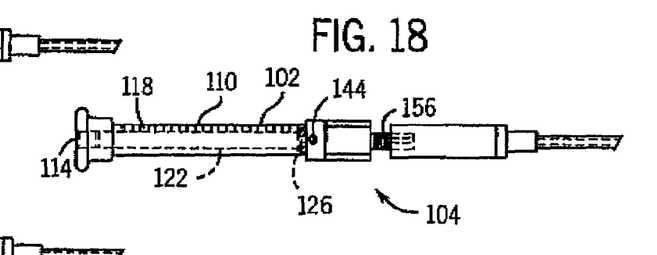
FIG. 18 is a side view rotated ninety degrees of the medical delivery system of FIG. 17 when properly connected.
Figure 19:
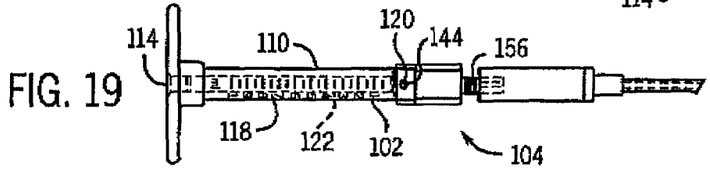
FIG. 19 is a side view of the medical delivery system of FIG. 16 when properly connected.

FIGS. 10-14 show various types of threaded sealing connections that may be incorporated into the present invention. FIGS. 10 and 11 show a standard threaded luer connection 232, including a stain relief portion 148 and a luer end 170. FIGS. 12-14 disclose modified luer connections 132, including modified luer connections with straight lead-ins but having a smaller diameter than the luer 232 in FIGS. 10 and 11 (FIG. 12), a modified luer connector with a straight lead with the initial outer thread removed (FIG. 13); and a modified luer connection with a straight lead with the outer thread remaining in place and the end tapered, shown in FIG. 14. A variety of types of connections could also be used as would be understood by one of ordinary skill in the art.

Depending upon the nature and type of threads 126, the number of indicator marks 120 on the syringe body 110 may also vary. For example, if a single lead thread is used, only one indicator mark 120 is required on the syringe. If a double lead thread is used, however, two of the indicator marks 120 must be incorporated onto the syringe body 110, each being approximately 180° from the other. In this case, the medical delivery or extraction system 100 would be properly connected when either of the indicator marks 120 is aligned with the viewing region 144. If a triple lead thread is used, three indicator marks 120 would be used with each of the indicator marks 120 being approximately 120° from the other indicator marks 120. In general, the number of indicator marks needed would correlate to the number of thread leads used.

Figures 5, 6, 7, 8, 9:
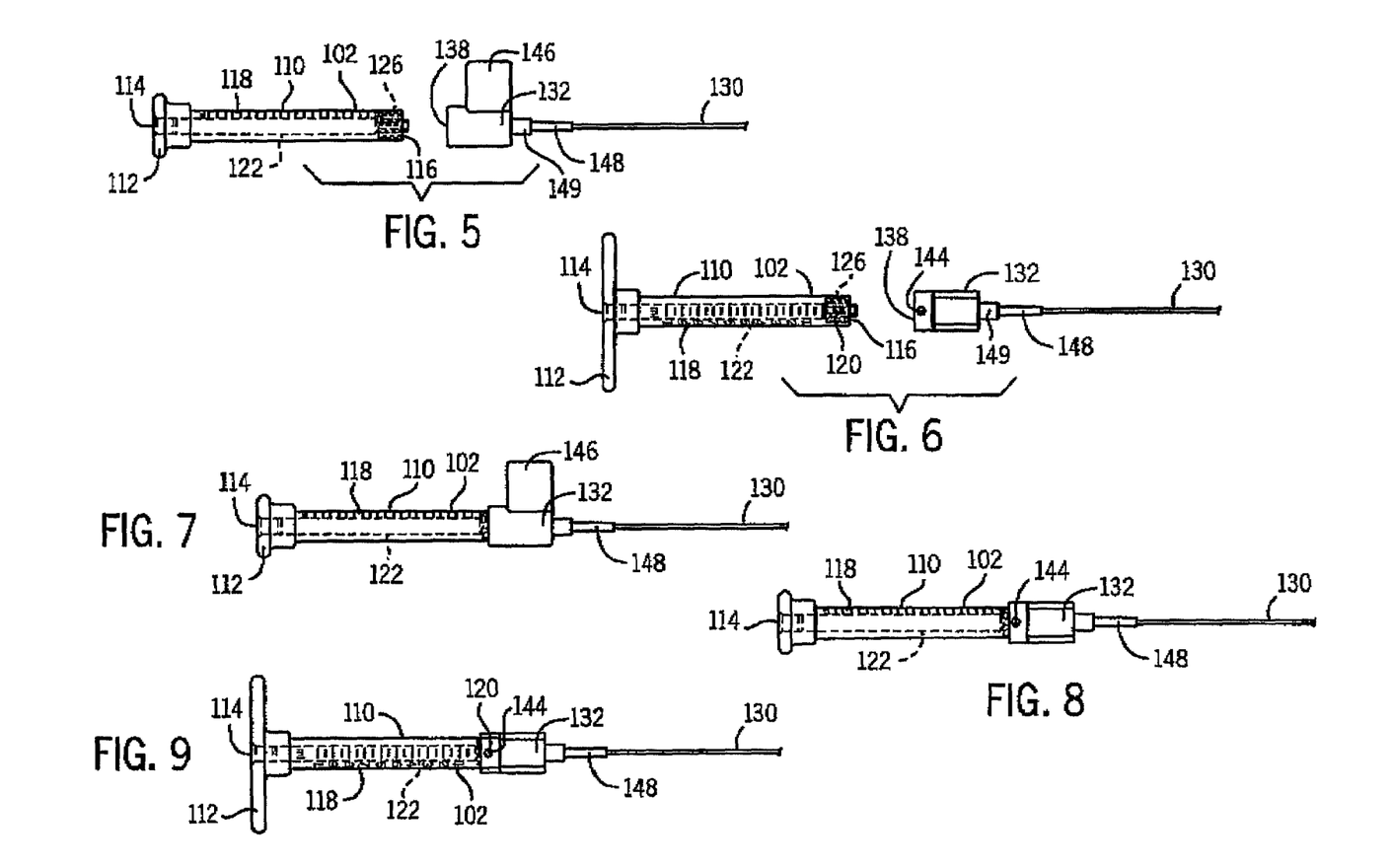
FIG. 5 is a side view of a needle assembly and syringe before being fastened.
FIG. 6 is a side view rotated ninety degrees of the needle assembly and syringe of FIG. 5.
FIG. 7 is a side view rotated ninety degrees of the needle assembly and syringe of FIG. 5 as the needle assembly is partially fastened to the syringe.
FIG. 8 is a side view of the needle assembly and syringe of FIG. 5 as the needle assembly is properly connected to the syringe.
FIG. 9 is a side view rotated ninety degrees of the needle assembly and syringe of FIG. 8 as the needle assembly is properly connected to the syringe.

The operation of the medical delivery or extraction system 100 is generally as follows. As shown in FIGS. 5 and 6, the needle assembly 104 is separable from the syringe 102. If the user desires to couple the noodle assembly 104 to the syringe 102, the user brings the second end 138 of the luer connection 132 towards the needle assembly receiving end 116 of the syringe body 110. When the second end 138 of the luer connection 132 comes into contact with the needle assembly receiving end 116 of the syringe body 110, the user either twists the gripping portion 146 of the luer connection 132 or grips the gripping portion 146 of the luer connection 132 and twists the syringe body 110. The mating action of the threads 126 with hub threads 170 causes the luer connection 132 to couple to the syringe body 110. As is shown in FIGS. 7-9, the connection between the luer connection 132 and the syringe body 110 becomes more pronounced as the luer connection 132 is twisted relative to the syringe body 110. As is shown in FIG. 7, when the luer connection 132 is only partially upon the syringe body 110, the indicator mark 120 is not yet visible through the viewing region 144. As the user continues to twist the luer connection 132, the indicator mark 120 ultimately aligns with the viewing region 144, as best shown in FIG. 9. At this position a proper connection has been achieved between the needle assembly 104 and the syringe 102, and the user is given an indication that additional tightening is not necessary. The user is then able to perform the particular procedure using the medical delivery or extraction system 100. When the user desires to remove the needle assembly 104 from the syringe 102, the user simply rotates the luer connection 132 in the opposite direction using the gripping portion 146.

The delivery or extraction system 100 of the present invention can be used in virtually any situation that requires an indication and assurance of a proper connection for rotationally connected medical delivery or extraction devices. Such environments range from sterile hospital suites to non-sterile doctors' offices. The system 100 could be used at ambient conditions in addition to hot or below freezing conditions and dry or humid conditions. The system 100 can also be packaged and sterilized using conventionally known methods and can be provided and used for non-sterile applications. The individual components can all be manufactured using conventionally known techniques resulting in a relatively low cost.

As mentioned previously, a variety of indicia can be used for indicating that the syringe 102 is properly connected to the needle assembly 104. For example, a variety of visual indicators could be used, and it is also possible to have an audible indication of a proper connection. This can be accomplished using a form of snap fitting in a mechanical design, an electronic computer chip in an electrical design, or other design systems. A combination of visual and audio indications could also be used. Furthermore, a number of the individual components can be replaced and/or modified depending upon the particular needs. For example, the syringe 102 could be in the form of a container such as a cartridge, vial or bottle, while the needle assembly 104 could be replaced with a different type of mechanism or device. Different types of seal interfaces, such as tapered seals, face seals, etc., could be used to ensure a secure connection, and connections other than luer connections could be used. For example, a variety of types of threads or a twist locking mechanism could be incorporated into the system 100.

It should be understood that the above description of the invention and specific examples and embodiments, while indicating the preferred embodiments of the present invention, are given by demonstration and not limitation. Many changes and modifications within the scope of the present invention may therefore be made without departing from the spirit thereof and the present invention includes all such changes and modifications.

What is claimed is:

1. A medical delivery or extraction system, comprising:
    a needle assembly including a hub, the hub having a verification component and, the hub having a needle connected thereto;
    a syringe body rotatably and threadably coupled to the needle assembly, an end of the syringe body at least partially disposed within or over the hub; and
    at least one indicium on the syringe body, the indicium and verification component each configured to travel a spiral path relative to each other as the threadably coupled syringe body and needle assembly are rotated relative to each other,
    the path of travel of the indicium and the path of travel of the verification component overlapping at a point where the at least one indicium aligns with the verification component at a single concurrent angular and linear orientation denoting a specific desired degree of tightening between the syringe body and the needle assembly representing the presence of a secure connection between the syringe body and the needle assembly, the syringe body and needle hub being retainable in the single concurrent angular and linear orientation.

2. The system of claim 1, wherein the syringe body includes a thread on an inner surface thereof, and wherein the hub includes a ridge for mating with the thread.

3. The system of claim 2, wherein the syringe body includes a triple lead thread for mating with the needle assembly, and wherein first, second and third indicia are positioned on the outer surface of the syringe body such that the syringe body is rotatably and properly connected to the needle assembly when the verification component is associated with any of the first, second or third indicia.

4. The system of claim 1, wherein the syringe body includes a double lead thread for mating with the needle assembly, and wherein first and second indicia are positioned on the outer surface of the syringe body such that the syringe body is rotatably and properly connected to the needle assembly when the verification component corresponds to either the first indicium or the second indicium.

5. The system of claim 1, wherein the syringe body includes a luer fitting on the inside thereof, the luer fitting mating with the hub.

6. The system of claim 1, wherein the indicium comprises a colored indicator.

7. The system of claim 6, wherein the verification component comprises an opening to view the indicium within the hub.

8. The system of claim 1, wherein the indicium snap fits with the verification component when the syringe body is properly connected to the needle assembly.

9. The system of claim 1, wherein the verification component comprises at least one of a visual or an audible verification.

10. The system of claim 9, wherein the verification component comprises a visual verification.

11. A delivery or extraction system, comprising:
    a fluid container having a first end and a second end, the second end including a marker;
    a delivery or extraction conduit having a first end and a second end, and including a verification component substantially adjacent the first end; and
    means for rotatably coupling the second end of the fluid container to the first end of the delivery or extraction conduit, the marker and verification component each configured to travel a spiral path relative to each other as the fluid container and delivery or extraction conduit are rotated relative to each other, the marker corresponding to the verification component when the fluid container is properly connected at a single concurrent angular and linear orientation denoting a specific desired degree of tightening between the fluid container and conduit, the desired concurrent angular and linear orientation representing the presence of a secure connection between the fluid container and the delivery or extraction conduit.

12. The system of claim 11, wherein the fluid container comprises a syringe with a luer connection thereon, the luer connection mating with the delivery or extraction conduit.

13. The system of claim 12, wherein the delivery or extraction conduit comprises a needle mounted upon a luer connection, the luer connection including a channel that mates with the luer connection when the fluid container is properly connected to the delivery or extraction conduit.

14. The system of claim 13, wherein the marker comprises a visual indicator.

15. The system of claim 14, wherein the visual indicator comprises a colored region at one end of the fluid container.

16. The system of claim 15, wherein the verification component comprises an opening on the luer connection, and wherein at least a portion of the colored region is visible through the opening when the fluid container is properly connected to the delivery or extraction conduit.

17. An injection or extraction system, comprising:
- a syringe with a threaded connection joint at one end thereof;
- a needle assembly with a channel therethrough for mating with the connection joint and including a verification component thereon, the verification component configured to be disposed over and visually expose a visual indicator when the syringe is properly connected to the needle assembly; the visual indicator on the syringe in the vicinity of the connection joint; and
- the disposition of the verification component over the visual indicator indicating that the needle assembly is rotatably and properly connected at a desired concurrent angular and linear orientation relative to the syringe and that additional tightening of the needle assembly is not necessary, the indication means positioned on the syringe and providing the indication when corresponding to the verification component, the desired concurrent angular and linear orientation representing the presence of a secure connection between the syringe body and the needle assembly.

18. The system of claim 17, wherein the connection joint comprises a single lead thread.

19. The system of claim 17, wherein the connection joint comprises multiple lead threads.

20. The system of claim 17, wherein the indicating means comprises:
- a region within the needle assembly that permits the user to view the visual indicator when the syringe is properly connected to the needle assembly.

21. The system of claim 20, wherein the region within the needle assembly comprises an opening through which at least a portion of the visual indicator is viewable when the syringe is properly connected to the needle assembly.

22. The system of claim 17, wherein the needle assembly comprises:
- a needle; and
- a luer connection including a channel that mates with the needle.

23. The system of claim 17, wherein the indicating means comprises means for indicating differing degrees of connection between the syringe and the needle assembly.

24. The system of claim 17, wherein the indicating means includes a viewing hole positioned on either a hub on the needle assembly or a gripping arm on the needle assembly.

25. A medical delivery or extraction system, comprising:
- a needle assembly including a hub, the hub having a needle connected thereto;
- a syringe body, having a threaded path and rotatably coupled to the needle assembly, the syringe body including a verification component, the verification component comprising a window through which at least one indicium is viewable when the syringe body and needle assembly are positioned at a desired linear and angular orientation along the threaded path; and the at least one indicium on the needle assembly,
- wherein the indicium corresponds to the verification component on the syringe body, when the syringe body is properly connected concurrently at both the desired angular and linear orientation relative to the needle assembly, the desired concurrent angular and linear orientation representing the presence of a secure connection between the syringe body and the needle assembly.

26. The system of claim 25, wherein the needle is separate from the syringe body.

\* \* \* \* \*

UNITED STATES PATENT AND TRADEMARK OFFICE
CERTIFICATE OF CORRECTION

PATENT NO. : 7,527,610 B2
APPLICATION NO. : 10/113680
DATED : May 5, 2009
INVENTOR(S) : Erickson It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 499 days Delete the phrase "by 499 days" and insert -- by 659 days --

Signed and Sealed this

Twenty-fourth Day of August, 2010

David J. Kappos
*Director of the United States Patent and Trademark Office*